United States Patent [19]

Grisar et al.

[11] 4,055,561
[45] Oct. 25, 1977

[54] α-ALKYLBENZYL LACTAMIMIDES

[75] Inventors: J. Martin Grisar; George P. Claxton; Robert D. MacKenzie, all of Cincinnati, Ohio

[73] Assignee: Richardson-Merrell Inc., Wilton, Conn.

[21] Appl. No.: 354,443

[22] Filed: Apr. 25, 1973

[51] Int. Cl.² .................. C07D 223/12; A61K 31/55; C07D 207/22; C07D 211/72
[52] U.S. Cl. .......................... 260/239 B; 260/239 BF; 260/293.62; 260/293.78; 260/296 R; 260/296 B; 260/326.5 L; 260/326.85; 260/326.9; 260/570.5 R; 542/449; 542/459; 424/244; 424/267; 424/274; 542/429

[58] Field of Search ........ 260/239 BE, 239 B, 326.85, 260/326.5 L, 293.78, 564 R, 564 RF, 293.62, 326.5 CA

[56] References Cited

U.S. PATENT DOCUMENTS 3,887,569  6/1975  Poos .................................. 260/239 B

FOREIGN PATENT DOCUMENTS 850,116  8/1970  Canada ............................ 260/239 B Primary Examiner—Donald G. Daus
Assistant Examiner—Mark L. Berch
Attorney, Agent, or Firm—William J. Stein; Eugene O. Retter; George W. Rauchfuss, Jr.

[57] ABSTRACT

Novel derivatives of α-alkylbenzyl lactamimide are useful as anticoagulants.

3 Claims, No Drawings

α-ALKYLBENZYL LACTAMIMIDES

FIELD OF THE INVENTION

This invention relates to substituted α-alkylbenzyl lactamimide derivatives, their preparation and their use as an anticoagulant on blood platelets.

DESCRIPTION OF THE PRIOR ART

The closest art known to applicants is Canadian Pat. No. 850,116, which discloses 1-lower alkyl-2-aralkylimino-methyleneimines having the formula

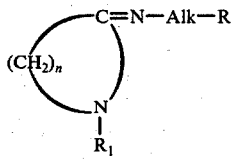

in which Alk represents cyclopropyl or a straight or branched alkylene chain having from 1 to 3 carbon atoms; R is phenyl or a substituted phenyl; $R_1$ is lower alkyl, benzyl; and n is an integer from 3 to 5. The compounds of the present invention differ in that the aromatic phenyl portion of the molecule is not substituted with a lower alkyl group or with a lower alkoxy group, but is substituted with higher alkyl groups having 8 to 14 carbon atoms. Moreover, the compounds of the prior art are stated to possess antiinflammatory activity, whereas still other members possess central nervous system activity. There is no disclosure of their usefulness as anticoagulants.

U.S. Pat. No. 3,378,438 discloses compounds having the structure

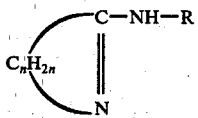

wherein R represents alkyl, cycloalkyl, aryl or an aralkyl radical which can be either substituted or unsubstituted. The compounds of the present invention are not included in the above generic formula. Furthermore, all of the compounds of the present invention contain a lower alkyl group having from 1 to 4 carbon atoms in the α-position of a substituted benzyl moiety, which is lacking in the prior art. The compounds of the reference patent are further stated to be useful as fungicidal agents. There is no disclosure that the prior art compounds are useful in preventing the coagulation of blood.

U.S. Pat. No. 3,894,002 describes substituted naphthylalkylene lactamimides having the formula:

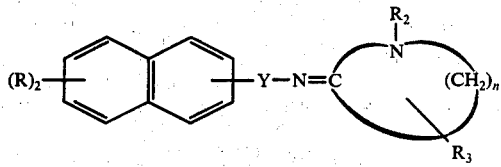

wherein each R group is hydrogen, halogen, trifluoromethyl, a straight or branched alkyl chain having from 1 to 12 carbon atoms, alkoxy or nitro, and where each R group may be the same or different; Y is a straight or branched alkylene chain having from 1 to 6 carbon atoms and is optionally substituted with phenyl or substituted phenyl wherein the substituents on the substituted phenyl are selected from halogen or lower alkyl having from 1 to 3 carbon atoms; $R_2$ is hydrogen or lower alkyl; $R_3$ is hydrogen or halogen; and n is an integer of from 3 to 11. Such compounds possess hypoglycemic, anticoagulant and diuretic activity. In contrast thereto the compounds of the present invention contain a substituted phenyl group and do not contain a naphthalene moiety. Additionally, the instant compounds are distinguished by the presence of a lower alkyl group in a position which is alpha to the benzyl moiety, which is not present in the prior art. Lastly, the compounds of the present invention are specific in their activity, i.e., they are useful mainly as anti-coagulants and devoid of hypoglycemic or diuretic activity, thus enabling specific treatment without incurring more general side effects.

U.S. Pat. No. 3,783,162 discloses benzhydryllactamimide derivatives having the formula:

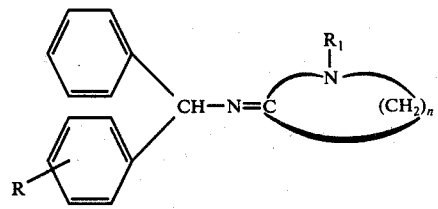

wherein R is hydrogen or lower alkoxy of from 1 to 6 carbon atoms; $R_1$ is hydrogen or lower alkyl having from 1 to 4 carbon atoms; and n is an integer of from 3 to 11. Such compounds possess both hypoglycemic and diuretic activity. In contrast thereto the compounds of the present invention differ in that they contain a lower alkyl group having from 1 to 4 carbon atoms in lieu of the unsubstituted phenyl radical of the prior art. Furthermore, the compounds of the present invention are useful as anticoagulants and possess little, if any, of the hypoglycemic and diuretic activity taught by the prior art.

SUMMARY OF THE INVENTION

This invention relates to novel α-alkylbenzyl lactamimides. More particularly, this invention relates to a class of substituted α-alkylbenzyl lactamimides which are useful in platelet aggregation. Still more particularly, the compounds of this invention are represented by the general formula:

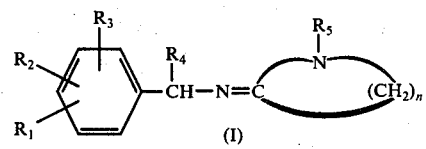

wherein
$R_1$ is selected from the group consisting of alkyl having from 8 to 14 carbon atoms, alkoxy having from 8 to 14 carbon atoms, cycloalkyl having from 5 to 14 carbon atoms, phenyl, phenoxy, phenylalkyl having from 1 to 4 aliphatic carbon atoms, phenylalkoxy having from 2 to 4 aliphatic carbon atoms, phenoxyalkoxy having from 2 to 4 aliphatic carbon atoms, 2-diphenylvinyl and fluoren-9-ylidenemethyl;

$R_2$ is selected from the group consisting of hydrogen or when taken together and adjacent to the group $R_1$ is the cyclic radical $-(CH_2)_3-$, $-CH_2CH_2C(CH_3)_2-$, $-(CH_2)_4-$ and $-C(CH_3)_2CH_2CH_2C(CH_3)_2-$;

$R_3$ is hydrogen or lower alkyl having from 1 to 4 carbon atoms;

$R_4$ is lower alkyl having from 1 to 4 carbon atoms;

$R_5$ is hydrogen or lower alkyl having from 1 to 4 carbon atoms; and $n$ is an integer of from 3 to 11; and the pharmaceutically acceptable acid addition salts thereof.

In general the compounds of this invention are prepared by reacting a substituted α-alkylbenzyl amine with a lactim ether to form a substituted α-alkylbenzyl lactamimide. Alternatively, the instant compounds may also be prepared by forming a lactam complex and reacting this complex with an appropriate primary amine.

A variety of compositions are also included within the scope of the present invention which are useful in preventing the coagulation of blood.

DETAILED DESCRIPTION OF THE INVENTION

For purposes of convenience and uniformity, all of the compounds of the present invention are represented as 2-substituted imino 1-azacycloalkanes as shown in Formula (I) above. Such compounds and their acid addition salts may also exist in their tautomeric form as illustrated by the following formula:

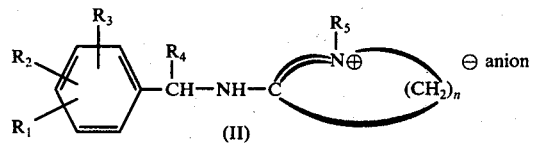

This tautomerism has been discussed by R. Kwok and P. Pranc, J. Org. Chem. 32, 740 (1967). When represented in this fashion, the compounds of the present invention would also be named differently, as for example, 2-(α-methyl-p-phenoxybenzylimino)hexahydro-1H-azepine would be named as 3,4,5,6-tetrahydro-7-[(α-methyl-p-phenoxy) benzylamino]-2H-azepine.

In solution under conditions of therapeutic utility, the proportion of each tautomeric form, as expressed by the delocalization of the positive charge between the two nitrogen atoms, will be dependent upon various factors including the nature of the side chain substituents, the pH of the medium, and temperature. This equilibrium state can be conveniently represented by the following formula:

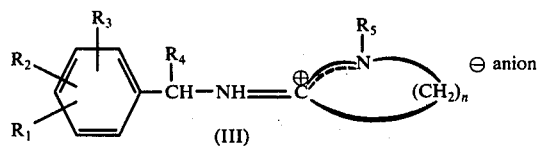

Thus, under a given set of conditions the instant compounds are present in either of their tautomeric forms as illustrated by Formulas (I) and (II), or in mixtures of these tautomeric forms, the compositions of which are dependent upon such factors as the nature of the various substituents and the physical environment of the molecule.

As can be seen in Formula (I) above, the compounds of the present invention are all substituted benzyl or phenylmethyl derivatives of various ring size lactamimides. Mandatory substitution occurs on the aliphatic or methyl portion of the benzyl radical and is limited to that of a lower alkyl group. This alkyl substituent, $R_4$, is either a straight or branched chain lower alkyl group having from 1 to 4 carbon atoms. Illustrative members of this group include the radicals methyl, ethyl, propyl, isopropyl and butyl. Additionally, the aromatic portion of the benzyl radical must be substituted as indicated by the symbol $R_1$. In general, the aromatic ring is monosubstituted. Substitution can occur at any position on the aromatic ring with substitution at the para position being preferred. The nature of the substituents varies over a wide range. Applicants have observed, however, that enhanced anticoagulant activity, devoid of hypoglycemic and diuretic side effects, is obtained in the presence of large lipophilic substituents on the aromatic portion of the benzyl nucleus. Thus, $R_1$ can represent a large straight or branched chain saturated alkyl group having from 8 to 14 carbon atoms. Illustrative of straight chain alkyl groups are octyl, nonyl, decyl, undecyl, dodecyl, tridecyl and tetradecyl radicals. Illustrative branched chain alkyl groups include the radicals 3,3-diethylpentyl, 4-ethyloctyl, 4-isobutyl-2,5-dimethylheptyl, and 4-propyl-2,3,3-trimethylpentyl or other combinations having from 8 to 14 carbon atoms. Such radicals may also be linked to the aromatic portion of the benzyl nucleus via an ether linkage. The symbol $R_1$ also represents a saturated cycloalkyl radical, as for example, the groups cyclopentyl, cycloheptyl, cyclononyl, cyclodecyl, cyclododecyl and cyclotetradecyl.

The symbol $R_1$ further represents certain unsaturated aromatic radicals as for example the phenyl and phenylalkyl radicals. In the latter instance, the aliphatic linkage between the phenyl group and the aromatic portion of the benzyl radical can be either saturated or unsaturated, branched or unbranched, having from 1 to 4 aliphatic carbon atoms. Such linking groups include the following radicals: methylene, ethylene, propylene, methylethylene, butylene, vinylene, propenylene and 2-butenyl. Various unsaturated aromatic radicals can also be linked to the aromatic portion of the benzyl nucleus via a simple ether linkage as in the phenoxy or phenylalkoxy substituents or via a diether linkage, as for example, in the phenoxyalkoxy radical. In such instances the aliphatic alkoxy linkage is limited to those alkoxy groups having from 2 to 4 aliphatic carbon atoms in order to exclude the unstable methane diether derivatives. These alkoxy groups are illustrated by the radicals: ethylene, propylene, methylethylene, butylene, methylpropylene and 1,1-dimethylethylene.

The symbol $R_2$ encompasses those compounds in which the aromatic portion of the benzyl group contains a fused 5 or 6 membered cycloalkyl ring to form an indane or tetralin moiety. Such rings can be further substituted in their aromatic portion with a lower alkyl group having from 1 to 4 carbon atoms as is represented by the symbol $R_3$. Illustrative of such lower alkyl groups are methyl, ethyl, propyl, isopropyl, butyl, sec.-butyl and tert.-butyl. Additionally, the saturated portion of these rings can be substituted with dimethyl groups in the 1-position of the indane nucleus and in the 1 and 4-positions of the tetralin nucleus.

The nitrogen atom in the lactam ring may be either unsubstituted or may be substituted with a lower alkyl group as represented by the symbol $R_5$, having from 1 to 4 carbon atoms. Illustrative of the members of this group are the radicals described in the aforementioned symbol $R_3$.

As seen in Formula (I) above, the lactamimide portion of the molecule may vary in ring size from that of a 5 to a 13-membered ring, one member of which must be nitrogen. Thus, the compounds of this invention include derivatives of pyrrolidine, piperidine, hexahydro-1H-azepine, octahydroazocine, octahydro-1H-azonine, azacyclodecane, azacycloundecane, azacyclododecane and azacyclotridecane.

A preferred sub-class of lactamimides is obtained wherein $R_1$ is phenyl, phenoxy, phenylalkyl having from 1 to 4 aliphatic carbon atoms, phenylalkoxy having from 2 to 4 aliphatic carbon atoms, and phenoxyalkoxy having from 2 to 4 aliphatic carbon atoms; $R_3$ and $R_5$ is hydrogen; $R_4$ is methyl and $n$ is the integer 5. These 2-[α-methyl(aromatic substituted)benzyl]hexahydro-1H-azepines are characterized by having good anticoagulant activity while being devoid of diuretic and hypoglycemic activity.

Illustrative of specific compounds which are encompassed by Formula (I) above are: 2-[(p-decyl-α-methylbenzylimino]pyrrolidine, 1-methyl-2-[α-methyl-p-(3,3-diethylpentyl)-benzylimino]pyrrolidine, 1-ethyl-2-[p-(dodecyloxy)α-methylbenzylimino]piperidine, 2-[α-methyl-p-(3,7-dimethyloctyloxy)-benzylimino]piperidine, 1-propyl-2-[α-butyl-p-cyclohexybenzylimino]hexahydro-1H-azepine, 2-[α-methyl-p-cyclododecylbenzylimino]hexahydro-1H-azepine, 2-[p-(2,2-diphenylvinyl)-α-isopropylbenzylimino]hexahydro-1H-azepine, 2-[1-(1,2,3,4-tetrahydro-6-naphthyl)-ethylimino]hexahydro-1H-azepine, hexahydro-2-[α,2-dimethyl-4-(3-phenoxypropoxy)benzylimino]-1H-azepine, 2-[α,5-dimethyl-2-(3-phenylethoxy)benzylimino]hexahydro-1H-azepine, 2-[α-3-dimethyl-4-(3-phenylpropoxy)benzylimino]-hexahydro-1H-azepine, hexahydro-2-[1-(4-indanyl)ethyl-imino]-1H-azepine, 1-methyl-2-[α-methyl-p-phenoxybenzyl-imino]hexahydro-1H-azepine, 2-[α-methyl-p-(3-phenyl-1-propen-1-yl)benzylimino]hexahydro-1H-azepine, 2-[α-methyl-p-(4-phenylbutoxy)-benzylimino]azacyclododecane, 2[p-(2-phenoxyethoxy)-α-methylbenzylimino]azacyclotridecane.

The expression "pharmaceutically acceptable acid addition salts" refers to any non-toxic organic or inorganic acid addition salts of the base compounds represented by Formula I. Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include the mono, di and tricarboxylic acids. Illustrative of such acids are, for example, acetic, propionic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids such as methanesulfonic acid and 2-hydroxyethenesulfonic acid. Either the mono or the di-acid salts can be formed, and such salts can be utilized in either a hydrated or a substantially anhydrous form.

In general the α-alkylbenzyl lactamimides of the present invention are prepared by reacting an excess amount of a lactim ether with a primary amine, as illustrated in the following reaction scheme:

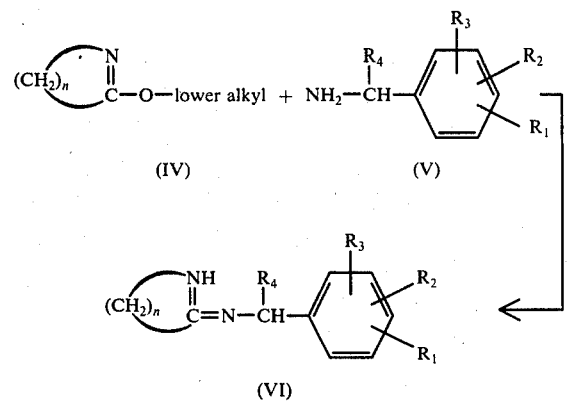

wherein the symbols $R_1$, $R_2$, $R_3$, $R_4$ and $n$ have the values previously assigned. The reaction is conducted in a manner similar to that reported by R. E. Benson and T. L. Cairns, J. Am. Chem. Soc. 70, 2115-8 (1948), and may be carried out either in the presence or in the absence of a solvent. Suitable solvents include the lower alcohols such as methanol or ethanol, benzene, toluene and the like, with the lower alcohols being the solvents of choice. A basic or acidic catalyst such as a tertiary amine or hydrogen chloride may be added to the reaction mixture. In general the hydrochloride salt of the reactant primary amine is preferred for use in this reaction. The temperature of the reaction mixture may vary from −40° to 180° C., preferably the temperature ranges from about 15° to 25° C. The reaction time may vary from a period of from about 1 hour to about 60 days depending upon the temperature of the reaction, the reactant primary amine, and more particularly the degree of steric hindrance of the amine, inasmuch as highly sterically hindered amines react much more slowly.

The lactim ethers (IV) which find use in this reaction may be prepared from corresponding commercially available lactams by methods known in the art. For example, the reaction of an appropriate lactam with dimethyl sulfate in a solvent such as benzene, toluene, xylene or the like at the reflux temperature of the particular solvent selected for a period of from 2 to 24 hours results in the formation of the corresponding 0-methyl-lactim ether.

The primary amines which find use in the present invention, either as the free base or the hydrochloride salt, may be prepared by several known methods. These amines can be obtained by the Leuckart reaction, whereby the appropriate acetophenone derivative is heated with ammonium formate to a temperature of from about 180°-200° C. for a period ranging from 2 to 12 hours to form the desired amine. The alkyl, cyclohexyl, phenyl, phenoxy or phenylalkyl substituted acetophenones may be obtained by a standard Friedel-Crafts acylation of the appropriately substituted benzene derivative. The alkoxy, phenylalkoxy and phenoxyalkoxy substituted acetophenones may be obtained by reaction of 2′,3′- or 4′-hydroxyacetophenone with alkyl, phenylalkyl or phenoxyalkyl halide in the presence of base. Alternatively, the acetophenones may be obtained by reaction of methyl magnesium halide with an appropriately substituted benzonitrile. The Grignard complex formed may also be reduced in situ with lithium aluminum hydride to the amine thereby avoiding the Leuckart reaction.

Similarly the above reaction may be carried out by using known thiolactim ethers such as S-methylthiocaprolactim [H. Behringer and H. Meier, Ann. 607, 67-91 (1957)], or by using thiolactams wherein it may be advantageous to employ a catalyst such as mercury, silver oxide or cyanide [J. A. Gautier and J. Renault, C. R. Acad. Sci. 234, 2081 (1952)].

The compounds of this invention may also be prepared using a complex of an appropriate lactam with phosphorous oxychloride, phosgene, borontrifluoride etherate, dimethyl sulfate, hydrogen halide or a combination of two or more such reagents. This reaction has been studied by H. Bredereck in a series of articles in Chem. Ber., 1953-1968, particularly volume 94, 2278 (1961) and volume 97, 1403 (1964). The complex formed is reacted with an appropriate primary amine described hereinabove in an aromatic hydrocarbon solvent such as benzene, toluene or xylene or an alkyl polyhalide solvent such as carbon tetrachloride, chloroform, methylene chloride, tetrachloroethylene or the like. The reaction temperature is limited by the boiling point of the solvent, however, in some cases it is advantageous to carry out the reaction at room temperature or with cooling at 0° to −40° C. depending on the reactants. This reaction is particularly suitable for the preparation of lactamimides in which the symbol $R_5$ is lower alkyl. Compounds in which the lactamide ring is piperidine may be conveniently prepared by catalytic hydrogenation of an appropriate amino pyridine derivative as described by T. B. Grave, J. Am. Chem. Soc. 46, 1460 (1924), M. Freifelder et al., J. Org. Chem. 29, 3730 (1964) and L. Birkofer, Ber. 75, 429 (1942).

The compounds of the present invention, including their acid addition salts and isomers, are useful as anticoagulants. They affect the coagulation of blood by preventing the aggregation of blood platelets. The blood platelets play a dominant role in thrombotic conditions, both in the initial event and at the occlusive stage. Arterial thrombosis, particularly in arteries supplying the heart muscle and brain, is a leading cause of death and disability. The compounds of the present invention can be administered to animals, mammals and humans, either per se or in combination with conventional pharmaceutical carriers in dosage unit forms. Suitable dosage unit forms include oral preparations such as tablets, capsules, powders, granules, oral solutions and suspensions, sublingual and intrabuccal preparations, as well as parenteral dosage unit forms which are useful for subcutaneous, intramuscular or intravenous administration. The quantity of active ingredient administered can vary over a wide range so as to provide from about 1.0 mg/kg to about 100 mg/kg of body weight per day in order to achieve the desired effect. Each unit dose can contain from about 5 to 500 mg of the active ingredient in combination with the pharmaceutical carrier. Such doses may be administered from 1 to 4 times daily.

In preparing solid compositions such as tablets, the principal active ingredient is mixed with conventional pharmaceutical excipients such as gelatin, starches, lactose, magnesium stearate, talc, acacia, dicalcium phosphate and functionally similar materials. Tablets can be laminated, coated or otherwise compounded to provide for a prolonged or delayed action and to release a predetermined successive amount of medication. Capsules are prepared by mixing the active ingredient with an inert pharmaceutical filler or diluent and filled in either hard gelatin capsules or machine encapsulated soft gelatin capsules. Syrups or elixirs can contain the active ingredients together with sucrose or other sweetening agents, methyl and propyl parabens as preservatives, and suitable coloring and flavoring agents.

Parenteral fluid dosage forms are prepared by utilizing the active ingredient in a sterile liquid vehicle, the preferred vehicle being water or a saline solution. Compositions having the desired clarity, stability and adaptability for parenteral use are obtained by dissolving from about 0.1 mg to about 3 grams of the active ingredient in a vehicle consisting of a mixture of nonvolatile liquid polyethylene glycols which are soluble in both water and organic liquids, and which have molecular weights ranging from about 200 to about 1500. Such solutions may advantageously contain suspending agents, such as sodium carboxymethylcellulose, methylcellulose, polyvinylpyrrolidone or polyvinyl alcohol. Additionally, they may contain bactericidal and fungicidal agents, as for example, parabens, benzyl alcohol, phenol or thimerosal. If desired, isotonic agents can be included, such as sugar or sodium chloride, as well as local anesthetics, stabilizing or buffering agents. In order to further enhance stability, the parenteral compositions may be frozen after filling and water removed by freeze-drying techniques well known in the art, enabling such dry, lypohilized powders to be reconstituted immediately prior to their use.

The following preparation and examples are illustrative of the novel compounds of the present invention and their compositions, but are not to be construed as necessarily limiting the scope thereof.

EXAMPLE I

α-Methyl-p-phenethylbenzylamine hydrochloride

A mixture of 87.5 g (0.39 mole) of 4'-phenethylacetophenone, M.P. 67°-70° C., prepared according to R. E. Lutz et al., J. Org. Chem. 12, 617 (1947), and 98.5 g (1.56 mole) of ammonium formate is slowly heated to 150° C. with stirring. After the initial foaming has subsided the temperature of the heating bath is raised to 185°-190° C. for a period of 4 hours. Upon cooling, the mixture is treated with several portions of water. To the residue is added 75 ml of concentrated HCl. The mixture is refluxed for 2 hours and is allowed to cool. The resulting solid is collected, washed with several portions of benzene and is recrystallized from isopropanol containing about 5% of water to yield 74.0 g (73% yield) of the desired product, M.P. 212°-214° C.

Following essentially the same procedure but substituting for the 4'-phenethylacetophenone an appropriate molar amount of the following ketones, resulted in the formation of the amine-hydrochlorides indicated:

TABLE 1

| Ketone | Amine Hydrochloride | M.P. |
|---|---|---|
| 4'-Tridecyl-acetophenone | α-Methyl-p-tridecyl-benzylamine | 110-2° C |
| 4'-Dodecyloxy-acetophenone | p-Dodecyloxy-α-methylbenzylamine | 99-112° C |
| 4'-Cyclohexyl-acetophenone | p-Cyclohexyl-α-methylbenzylamine | 232-6° C (dec.) |
| 4'-Phenyl-acetophenone | α-Methyl-p-phenyl-benzylamine | 223-6° C |
| 4'-Phenoxy-acetophenone | α-Methyl-p-phenoxy benzylamine | 196-9° C |
| 4'-(2,2-Diphenylvinyl)-acetophenone | p-(2,2-Diphenylvinyl)-α-methylbenzylamine | 238-42° C |
| 4-acetyl-1,1- | 4-(α-Aminoethyl)-1,1- | 254-5° C |

TABLE 1-continued

| Ketone | Amine Hydrochloride | M.P. |
|---|---|---|
| dimethyl-6-tert.-butylindane | dimethyl-6-tert.-butylindane | (dec.) |
| 7-acetyl-6-ethyl-1,1,4,4-tetramethyl-1,2,3,4-tetrahydronaphthalene | 7-(α-Aminoethyl)-6-ethyl-1,1,4,4-tetramethyl-1,2,3,4-tetrahydronaphthalene | 261–3° C (dec.) |

EXAMPLE II

4'-(3-Phenylpropoxy)acetophenone

A mixture of 68.1 g (0.5 mole) of 4'-hydroxyacetophenone, 100.3 g (0.5 mole) of 3-phenylpropyl bromide, 69.0 g (0.5 mole) of potassium carbonate and 500 ml of anhydrous acetone is refluxed with stirring for 8 hours. After adding 1 liter of water the product is extracted into ether, the extract is washed with water and 2 N sodium carbonate solution and dried over anhydrous sodium sulfate and the solvent is evaporated. The resulting oil (125.8 g) begins to crystallize and yields after two recrystallizations from ether-hexane and ether, respectively, 73.9 g (58% yield) of the desired product, M.P. 80°–81°.

Following essentially the same procedure, the following reactants were substituted for the 4'-hydroxyacetophenone and 3-phenylpropyl bromide:

4'-hydroxyacetophenone and 3-phenoxypropyl bromide
3'-hydroxyacetophenone and 4-phenoxybutyl bromide
2'-hydroxyacetophenone and phenethyl bromide These reactants resulting in the formation of the following products, respectively: 4'-(3-Phenoxypropoxy)acetophenone, M.P. 78°–79° C., 3'-(4-Phenoxybutoxy)acetophenone, M.P. 60°–61° C., and 2'-(2-Phenylethoxy)acetophenone, M.P. 40°–43° C.

EXAMPLE III p-(Fluoren-9-ylidenemethyl)-α-methyl-benzylamine hydrochloride

A hot solution of 100.0 g of α-fluoren-9-ylidene-p-tolunitrile, prepared as described by R. E. Allen et al., J. Amer. Chem. Soc. 80, 591 (1958), in 2 liter of toluene is added rapidly to methylmagnesium iodide (prepared from 82.0 g of methyl iodide in ethyl ether) in 1 liter of toluene. After refluxing for 2 hours, the mixture is decomposed with 3 N HCl. The crude product is recrystallized from acetonitrile to yield 87.1 g (82% yield) of 4'-fluoren-9-ylidenylmethylacetophenone, M.P. 123°–126° C.

Following essentially the same procedure as in Example I but substituting 4'-fluoren-9-ylidenylmethylacetophenone for the 4'-phenethylacetophenone resulted in the formation of p-(fluoren-9-ylidenemethyl)-α-methylbenzylamine hydrochloride having a M.P. 259°–61° C. (dec.)

EXAMPLE IV

Hexahydro-2-(α-methyl-p-phenethylbenzylimino)-azepine hydrochloride

A mixture of 15.0 g of α-methyl-p-phenethylbenzylamine hydrochloride and 25 ml of O-methylcaprolactim is stirred into a slurry and allowed to stand at room temperature for 4 days with occasional stirring. Small portions of absolute ethanol are added to keep the slurry stirrable. The mixture is then cooled to −20° C., the precipitate is collected, washed with small portions of absolute ether and recrystallized from a mixture of acetone-methanol to yield 15.7 g (76% yield) of the desired product, M.P. 230°–231.5° C.

EXAMPLE V 2-(α-Methyl-p-tridecylbenzylimino)hexahydro-1H-azepine hydrochloride Following essentially the same procedure described in Example IV but substituting α-methyl-p-tridecylbenzylamine hydrochloride for the α-methyl-p-phenethylbenzylamine hydrochloride above, results in the formation of 2-(α-methyl-p-tridecylbenzylimino)hexahydroazepine hydrochloride having a M.P. 183°–5° C.

EXAMPLE VI 2-(p-Dodecyloxy-α-methylbenzylimino)hexahydro-1H-azepine hydrochloride Following essentially the same procedure described in Example IV above and substituting p-dodecyloxy-α-methylbenzylamine hydrochloride for the α-methyl-p-phenyethylbenzylamine hydrochloride above, results in the formation of 2-(p-dodecyloxy-α-methylbenzylimino)hexahydroazepine hydrochloride having a M.P. of 186°–8° C. (dec.)

EXAMPLE VII 2-(p-Cyclohexyl-α-methylbenzylimino)hexahydro-1H-azepine hydrochloride Following essentially the same procedure described in Example IV above and substituting p-cyclohexyl-α-methylbenzylamine hydrochloride for the α-methyl-p-phenyethylbenzylamine hydrochloride above, results in the formation of 2-(p-cyclohexyl-α-methylbenzylimino)hexahydroazepine hydrochloride having a M.P. of 245°–7° C.

EXAMPLE VIII

2-[α-(4-Biphenylyl)ethylimino]hexahydro-1H-azepine hydrochloride

Following essentially the same procedure described in Example IV above and substituting α-methyl-p-phenylbenzylamine hydrochloride for the α-methyl-p-phenethylbenzylamine hydrochloride above, results in the formation of 2-[α-(4-biphenylyl)ethylimino]hexahydroazepine hydrochloride having a M.P. of 245°–7° C.

EXAMPLE IX 2-(α-Methyl-p-phenoxybenzylimino)-hexahydro-1H-azepine hydrochloride Following essentially the same procedure described in Example IV above and substituting α-methyl-p-phenoxybenzylamine hydrochloride for the α-methyl-p-phenethylbenzylamine hydrochloride above, results in the formation of 2-(α-methyl-p-phenoxybenzylimino)hexahydroazepine hydrochloride having a M.P. of 210°–2° C., (dec.)

EXAMPLE X

2-[p-(2,2-Diphenylvinyl)-α-methylbenzylimino]hexahydro-1H-azepine hydrochloride

Following essentially the same procedure described in Example IV above and substituting p-(2,2-diphenylvinyl)-α-methylbenzylamine hydrochloride for the α-methyl-*p*-phenethylbenzylamine hydrochloride above, results in the formation of 2-[*p*-(2,2-Diphenylvinyl)-α-methylbenzylimino hexahydroazepine hydrochloride having a M.P. of 219°-21° C.

EXAMPLE XI

2-[1-(6-Tert.-butyl-1,1-dimethyl-4-indanyl)ethylimino]-hexahydro-1H-azepine hydrochloride Following essentially the same procedure described in Example IV above and substituting 4-(α-aminoethyl)1,1-dimethyl-6-tert.-butylindane for the α-methyl-*p*-phenethylbenzylamine hydrochloride above, results in the formation of 2-[1-(6-tert.-butyl-1,1-dimethyl-4-indanyl)ethylimino]hexahydro-1H-azepine hydrochloride, having a M.P. of 257°-8° C. (dec.)

EXAMPLE XII

2-[1-(7-Ethyl-1,2,3,4-tetrahydro-1,1,4,4-tetramethyl-6-naphthyl)ethylimino]hexahydro-1H-azepine hydrochloride Following essentially the same procedure described in Example IV above and substituting 7-(α-aminoethyl)-6-ethyl-1,1,4,4-tetramethyl-1,2,3,4-tetrahydronaphthalene for the α-methyl-*p*-phenethylbenzylamine hydrochloride above, results in the formation of 2-[1-(7-ethyl-1,2,3,4-tetrahydro-1,1,4,4-tetramethyl-6-naphthyl)ethylimino]hexahydro-1H-azepine hydrochloride, having a M.P. of 246.5°-7.5° C. (dec.)

EXAMPLE XIII

Hexahydro-2-[α-methyl-*p*-(3-phenylpropoxy)benzylimino]azepine hydrochloride

Following essentially the same procedure described in Example I above but substituting 4'-(3-phenylpropoxy)acetophenone for the 4'-phenethylacetophenone results in the formation of *p*-(3-phenylpropoxy)-α-methylbenzylamine hydrochloride, M.P. 142°-5° C.

Substituting this amine for the α-methyl-*p*-phenethylbenzylamine of Example IV results in the formation of hexahydro-2-[α-methyl-*p*-(3-phenylpropoxy)benzylimino]azepine hydrochloride, having a M.P. of 202°-5° C.

EXAMPLE XIV

Hexahydro-2-[α-methyl-*p*-(3-phenoxypropoxy)benzylimino]-azepine hydrochloride

Following essentially the same procedure described in Example I above but substituting 4'-(3-phenoxypropoxy)acetophenone for the 4'-phenethylacetophenone results in the formation of α-methyl-*p*-(3-phenoxypropoxy)benzylamine hydrochloride, M.P. 71°-81° C.

Substituting this amine for the α-methyl-*p*-phenethylbenzylamine of Example IV results in the formation of hexahydro-2-[α-methyl-*p*-(3-phenoxypropoxyben-zylimino]azepine hydrochloride, having a M.P. of 162°-4° C.

EXAMPLE XV

2-[α-Methyl-m-(4-phenoxybutoxy)benzylimino]pyrrolidine hydrochloride

Following essentially the same procedure described in Example I above but substituting 3'-(4-phenoxybutoxy)acetophenone for the 4'-phenethylacetophenone results in the formation of α-methyl-m-(4-phenoxybutoxy)benzylamine hydrochloride, M.P. 79°-81° C.

Substituting this amine for the α-methyl-*p*-phenethylbenzylamine hydrochloride, and substituting O-methylbutyrolactim for the O-methylcaprolactim results in the formation of 2-[α-methyl-m-(4-phenoxybutoxy)benzylimino]pyrrolidine hydrochloride, having a M.P. of 136°-8° C. (dec.)

EXAMPLE XVI

Hexahydro-2-[α-methyl-o-(2-phenylethoxy)benzylimino]azepine hydrochloride

Following essentially the same procedure described in Example I above but substituting 2'-(2-phenylethoxy)acetophenone for the 4'-phenethylacetophenone results in the formation of α-methyl-o-(2-phenylethoxy)-benzylamine hydrochloride, M.P. 120°-133° C. (dec.)

Substituting this amine for the α-methyl-*p*-phenethylbenzylamine of Example IV results in the formation of hexahydro-2-[α-methyl-o-(2-phenylethoxy)benzylimino]azepine hydrochloride, having a M.P. of 189°-90° C. (dec.)

EXAMPLE XVII

1-Methyl-2-(α-methyl-*p*-phenethylbenzylimino)pyrrolidine hydrochloride

To 9.9 g (0.1 mole) of N-methyl-2-pyrrolidone in 200 ml of benzene is added dropwise 7.7 g (0.05 mole) of phosphorous oxychloride. The mixture is stirred at room temperature for a period of 4 hours. α-Methyl-*p*-phenethylbenzylamine hydrochloride, 13.1 g (0.05 mole), is added, the mixture stirred at room temperature for 1 hour and at its reflux temperature for an additional period of 4 hours. After cooling overnight, 2 N hydrochloric acid is added, the benzene layer separated and the aqueous layer made alkaline with 2 N NaOH. The product is extracted with ether, dried and upon removal of the solvent yielded 15.5 g of oil which is converted into its hydrochloride salt by the addition of HCl. After three recrystallizations from acetone, 5.8 g of the desired product is obtained, M.P. 87°-89° C.

EXAMPLE XVIII

2-[α-(4-Biphenylyl)ethylimino]azacyclotridecane hydrochloride

To 5.0 g (25 m mole) of 2-azatridecanone in 100 ml of benzene is added dropwise 3.9 g (25 m mole) of phosphorous oxychloride and the mixture stirred at room temperature for a period of 4 hours. α-methyl-*p*-phenylbenzylamine hydrochloride, 5.3 g (23 m mole), is added and stirred at room temperature for 1 hour and refluxed for an additional 4 hours. Hydrochloric acid, 2N, is added and the benzene layer separated, dried over sodium sulfate, and evaporated to dryness. The crude product is crystallized from acetone, M.P. 135°-142° C.

EXAMPLE XIX

2-[[1-[*p*-(Fluoren-9-ylidenemethyl)phenyl]ethylimino]-hexahydro-1H-azepine

Following essentially the same procedure described in Example IV above and substituting *p*-(fluoren-9-ylidenemethyl)-α-methylbenzylamine hydrochloride for the α-methyl-*p*-phenethylbenzylamine hydrochloride above results in the formation of 2-[[1-[*p*-(fluoren-9-ylidenemethyl)phenyl]ethylimino]]-hexahydro-1H-azepine, having a M.P. of 265.5°-7.5° C. (dec.)

EXAMPLE XX

The anticoagulant activity of the compounds of this invention is determined by the inhibition of platelet (white thrombus) aggregation, which is the initial phase involved in the coagulation of blood. Platelet-rich plasma, (PRP) obtained from a human volunteer, having a platelet count of approximately 400,000/mm$^3$ is caused to aggregate using a final concentration of 2 micrograms of adenosine diphosphate per ml of PRP. Quantitative platelet aggregation measurements are made using a photometer connected to an automatic recorder which measures the changes in optical clarity of a standard cell containing the test solution. As the platelets aggregate, light transmission increases and thus both the rate of aggregation and the degree of aggregation can be determined. In this fashion, adenosine diphosphate induced aggregation of platelet-rich plasma is compared under identical circumstances to a corresponding aliquot containing a dilute solution of the test compound. The results are expressed as a percent inhibition.

Following this procedure the compound 2-($\alpha$-methyl-$p$-phenethylbenzylimino)hexahydro-1H-azepine hydrochloride at concentrations of 100, 30 and 10 micrograms/milliliter demonstrates an in vitro inhibition of adenosine diphosphate induced platelet aggregation in human platelet-rich plasma of 78%, 37% and 8%, respectively.

EXAMPLE XXI

Preparation of a tablet formulation

One thousand tablets for oral use, each containing 25 mg of 2-($\alpha$-methyl-$p$-phenethylbenzylimino)hexahydro-1H-azepine hydrochloride are prepared according to the following formulation:

| | | Grams |
|---|---|---|
| (a) | 2-($\alpha$-methyl-$p$-phenethylbenzylimino)-hexahydro-1H-azepine hydrochloride | 25 |
| (b) | Dicalcium phosphate | 150 |
| (c) | Methylcellulose, U.S.P. (15 cps) | 6.5 |
| (d) | Talc | 20 |
| (e) | Calcium stearate | 2.5 |

The 2-($\alpha$-methyl-$p$-phenethylbenzylimino hexahydro-1H-azepine hydrochloride and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE XXII

Preparation of a capsule formulation

One thousand two-piece hard gelatin capsules for oral use each containing 100 mg of 2-($\alpha$-methyl-$p$-phenoxybenzylimino)hexahydro-1H-azepine hydrochloride are prepared from the following ingredients:

| | | Grams |
|---|---|---|
| (a) | 2-($\alpha$-methyl-$p$-phenoxybenzylimino)-hexahydro-1H-azepine hydrochloride | 100 |
| (b) | Lactose, U.S.P. | 100 |
| (c) | Starch, U.S.P. | 10 |
| (d) | Talc, U.S.P. | 5 |
| (e) | Calcium stearate | 1 |

The finely powdered materials are mixed until uniformly dispersed and filled into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE XXIII

Preparation of a parenteral solution

A sterile aqueous solution suitable for parenteral use is prepared from the following ingredients:

| | | Grams |
|---|---|---|
| (a) | 2-($\alpha$-methyl-$p$-phenoxybenzylimino)-hexahydro-1H-azepine hydrochloride | 1 |
| (b) | Polyethylene glycol 4000, U.S.P | 3 |
| (c) | Sodium chloride | 0.9 |
| (d) | Polyoxyethylene derivatives of sorbitan monooleate (TWEEN 80) U.S.P. | 0.4 |
| (e) | Sodium metabisulfite | 0.1 |
| (f) | Methylparaben, U.S.P. | 0.18 |

The parabens, sodium metabisulfite, and sodium chloride are dissolved in approximately one-half the volume of water for injection at 80° C. with stirring. The solution is cooled to below 40° C. and the active ingredient is dissolved therein followed by the polyethylene glycol 4,000 and the polyoxyethylene derivatives of sorbitan monooleate. The cooled solution is adjusted to the final volume with water for injection and is then sterilized by sterile filtration through a suitable filter. Each one ml of solution contains 10 mg of 2-($\alpha$-methyl-$p$-phenoxybenzylimino)hexahydro-1H-azepine hydrochloride as the active ingredient.

We claim:

1. An $\alpha$-methylbenzyl lactamimide having the formula $$R_2 \underset{R_1}{\overset{CH_3}{\underset{|}{\diagdown}}} \phantom{xx} \overset{H}{\underset{|}{\diagdown}} \phantom{x} CH-N=C \underset{(CH_2)_5}{\diagdown}$$

wherein
$R_1$ is phenyl, phenoxy, the group

[benzene ring]—$(CH_2)_m$— wherein $m$ is an integer of from 1 to 4, phenylalkoxy having from 2 to 4 aliphatic carbon atoms and phenoxyalkoxy having from 2 to 4 aliphatic carbon atoms;
$R_2$ is selected from the group consisting of hydrogen or when taken together and adjacent to the group $R_1$ is the cyclic radical —(CH$_2$)$_3$—, —CH$_2$CH$_2$C(CH$_3$)$_2$—, —(CH$_2$)$_4$— and —C(CH$_3$)$_2$CH$_2$CH$_2$C(CH$_3$)$_2$;
and the pharmaceutically acceptable acid addition salts thereof.

2. A compound of claim 1 which is 2-($\alpha$-methyl-$p$-phenoxybenzylimino)hexahydro-1H-azepine and its pharmaceutically acceptable acid addition salts.

3. A compound of claim 1 which is 2-($\alpha$-methyl-$p$-phenethylbenzylimino)hexahydro-1H-azepine and its pharmaceutically acceptable acid addition salts.

* * * * *

UNITED STATES PATENT AND TRADEMARK OFFICE
CERTIFICATE OF CORRECTION

PATENT NO. : 4,055,561
DATED : October 25, 1977
INVENTOR(S) : J. Martin Grisar, George P. Claxton and Robert D. MacKenzie It is certified that error appears in the above-identified patent and that said Letters Patent are hereby corrected as shown below:

Column 3, line 60, "NH══C" should read "NH═══C" and the correct formula should read as follows:

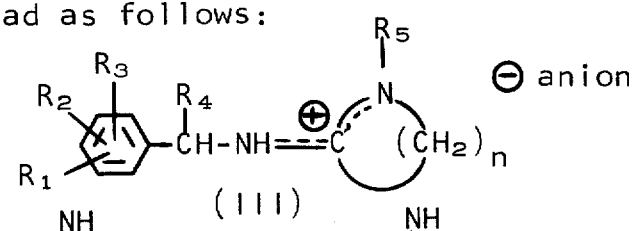

Column 6, line 15, "C═N" should read "C═N" and the correct formula should read as follows:

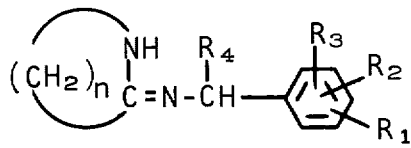

Column 14, line 23, items (g) and (h) were omitted and should read: (g) Propylparaben, U.S.P. ..... 0.02; (h) Water for injection q.s. to 100 ml.

Signed and Sealed this

Twenty-second Day of January 1980

[SEAL]

Attest:

SIDNEY A. DIAMOND

Attesting Officer

Commissioner of Patents and Trademarks